United States Patent [19]

Astoin et al.

[11] Patent Number: 4,477,453
[45] Date of Patent: Oct. 16, 1984

[54] OXIME ETHERS OF 1-PYRIDYL-3-PENTANONE

[75] Inventors: Jacques N. Astoin, Paris; Francis Lepage, Creteil; Jean-Pierre M. J. Fromantin, Versailles, all of France

[73] Assignee: Univablot, Paris, France

[21] Appl. No.: 423,104

[22] Filed: Sep. 24, 1982

[30] Foreign Application Priority Data

Dec. 11, 1981 [FR] France .................. 81 23147

[51] Int. Cl.³ .................... A61K 31/50; C07D 401/12
[52] U.S. Cl. ................................ 424/250; 424/263;
424/248.57; 546/281; 546/333; 546/338;
544/124; 544/360
[58] Field of Search .............. 546/338, 333, 281;
544/124, 360; 424/250, 263, 248.7

[56] References Cited

U.S. PATENT DOCUMENTS 3,733,359  5/1973  Hubele et al. ............... 546/338

FOREIGN PATENT DOCUMENTS 0007679  2/1980  European Pat. Off. .
1217007 12/1959  France .
2253505 12/1973  France .

Primary Examiner—Jane T. Fan
Attorney, Agent, or Firm—Wegner & Bretschneider

[57] ABSTRACT

The present invention relates to oxime ethers of the general formula I

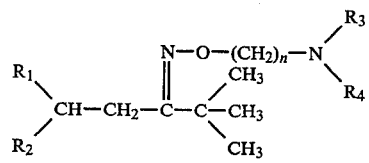

$R_2$ being a pyridyl radical.

The invention also relates to processes for the preparation of oxime ethers of general formula I.

The compounds according to the invention may be used as medicaments particularly for their spasmolytic and anti-histamine action.

9 Claims, No Drawings

OXIME ETHERS OF 1-PYRIDYL-3-PENTANONE

The present invention relates to oxime ethers of 1-pyridyl-3-pentanone, their preparation and their use as medicaments.

The compounds according to the present invention are of the general formula I

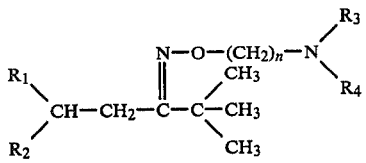

in which
R$_1$ is chosen from a cyclohexyl radical, or a phenyl or benzyl radical optionally substituted by a halogen atom or by a straight chain or branched alkyl radical having 1 to 4 carbon atoms,
R$_2$ is a pyridyl radical,
each of R$_3$ and R$_4$, which may be the same or different, represents a straight chain or branched alkyl radical having 1 to 4 carbon atoms, or
R$_3$ and R$_4$ together represent an alkylene chain having 4 to 7 carbon atoms which may also optionally contain an oxygen or nitrogen heteroatom, and
n is an integer of 1 to 4, as well as salts, quaternary ammonium derivatives, possible stereo-isomers and their mixture of the said oxime ethers.

The preferred compounds are those in which n is 2 or 3. Most particularly the preferred compounds are those in which n is 2 or 3 and R$_3$ and R$_4$ together represent an alkylene chain of 5 carbon atoms and R$_1$ is a phenyl radical.

The oxime ethers according to the invention likewise include all the possible stereo-isomers and mixtures of them.

The compounds of formula I may be prepared by the following processes:

According to a first process a ketone of general formula II

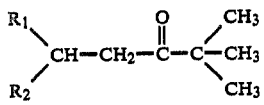

is reacted with a hydroxylamine derivative of general formula III

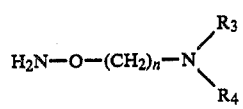

in which R$_1$, R$_2$, R$_3$, R$_4$ and n have the meanings given above, preferably in the presence of a solvent which is inert to the reaction, for example ethanol or pyridine.

According to a second process, an oxime of general formula IV

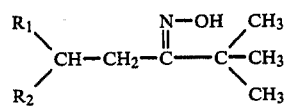

is reacted with a chlorine-containing derivative of an alkylamine of formula V

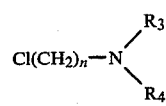

in which R$_1$, R$_2$, R$_3$, R$_4$ and n have the meanings given above. The reaction takes place in the presence of an inert solvent such as for example dimethylformamide, toluene or cumene in the presence of a basic condensation agent such as hydrides or amides of alkali metals such as sodium hydride.

The ketones of formula II may be obtained by the action of an organomagnesium compound of formula IV

$$R_1MgHal \qquad (VI)$$

on ketones of formula VII

The ketones of formula VII, of which some are for example described in French Pat. No. 7343940 published under the No. 2253505 may be obtained by condensing in aqueous or alcoholic media pinacolin (3,3-dimethyl-butanone) with an aldehyde of formula VIII

$$R_2-CHO \qquad (VIII)$$

In the formulae VI to VIII R$_1$ and R$_2$ have the meanings given above and Hal represents a halogen atom.

The compounds of formula I may be converted in known manner into their acid addition salts or into their quaternary ammonium salts.

The acid addition salts are prepared with physiologically acceptable acids such as citric acid, fumaric acid, acetic acid etc ...

In order to prepare the quaternary ammonium salts the compounds of general formula I are reacted with compounds suitable for their conversion into quaternary derivatives such as for example an alkyl halide or an ester of methane-sulfonic acid.

The compounds according to the invention as well as their physiologically acceptable addition salts may be used as medicaments particularly for their spasmolytic and anti-histamine action, for example for the treatment of cardio-vascular disorders.

The invention provides a method of treating a patient which method comprises administering to the patient in spasmolytic or anti-histamine effective amount at least one compound according to the invention.

The compounds according to the invention may be used in association with a pharmaceutically compatible excipient for oral administration for example in the form of tablets, lozenges or capsules and for parenteral administration in the form of injectable solutions for the soluble compounds and for endo-rectal administration in the form of suppositories.

The daily dosage is the order of 50 to 250 mg for oral administration and about 5 to 50 mg for administration by injection.

In order to show the spasmolytic effect, there is used the method of MAGNUS (Versuche am überbunden Dünndarm von Saugetieren. Arch. Gas. Physiol. 1904, 102-123). The anti-spasmodic activity is measured on the spasm provoked by acetylcholine or barium chloride in the isolated duodenum of the rat.

A rat is killed, after opening of the abdomen, the portion of the duodenum is withdrawn and is carefully washed with Tyrode solution at 37° C. The fragment of intestine is fixed in an isolated specimen chamber at 37° C. and oxygenated. There is determined the dose of acetylcholine or of barium chloride, expressed in moles per liter, which when added to the chamber provokes a contractile response in the organ providing a trace on paper in the recorder. After washing of the organ, there is determined the dose of the compound according to the present invention which when added to the chamber during one minute before the acetylcholine or barium chloride dose determined reduces the spasm by half. One operates in the same manner with a reference compound, atropine for acetylcholine and papaverine for barium chloride. One determines thus, for the test compound and the reference compound, the effective dose 50.

The anti-histamine action is demonstrated in the same manner using the isolated ileum of the guinea pig. The method is strictly the same only the contractural agent is changed. For this test it is histamine and the reference compound is promethazine.

Other advantages and characteristics of the invention will appear in the following Examples which are given by way of illustration.

EXAMPLE 1

1-Phenyl-1-(2-pyridyl)-4,4-dimethyl-3-pentanone and its oxime

There is added bit by bit an ethereal suspension of 0.13 mole 1-(2-pyridyl)-4,4-dimethyl-pent-1-en-3-one to a solution of phenyl magnesium bromide prepared from 0.17 mole bromobenzene, 0.17 gramme atom magnesium in 130 ml ether. This is maintained under reflux for half an hour. The product obtained is decomposed in acidulated water, extracted with ether, dried, then concentrated and recrystallised from petroleum ether. The yield is 87%. The corresponding 1-phenyl-1-(2-pyridyl)-4,4-dimethyl-3-pentanone oxime is prepared by reaction of 0.1 mole hydroxylamine hydrochloride with 0.1 mole of ketone in the presence of 0.5 mole sodium carbonate.

EXAMPLES 2 TO 6

The starting ketones of general formula II and the corresponding oximes of general formula IV are prepared according to a method analogous to that described in Example 1. The particular formulae of these ketones as well as their corresponding oximes of general formula IV are indicated with their physical constants in Table I below.

All the compounds 1 to 6 are assembled in Table I below together with their physical constants.

TABLE I

| Ex | Formulae II or V R₁ | R₂ | Ketone of formula II Boiling point Bp: °C./mm Hg and/or Melting point Mp: °C. | Oxime of formula IV |
|---|---|---|---|---|
| 1 | phenyl | 2-pyridyl | Bp: 138/0.03 | Mp: 158 |
| 2 | 4-chlorophenyl | 2-pyridyl | Bp: 174/0.12 | Mp: 92 |
| 3 | benzyl (C₆H₅CH₂–) | 2-pyridyl | Bp: 147/0.05 | Mp: 112 |
| 4 | cyclohexyl | 2-pyridyl | Bp: 154/0.05 | Mp: 124 |
| 5 | phenyl | 3-pyridyl | Bp: 156/0.05 Mp: 82 | Mp: 115 |
| 6 | phenyl | 4-pyridyl | Bp: 163/0.08 Mp: 78 | Mp: 142 |

EXAMPLE 7

O-Diethylaminoethyl ether of the oxime of 1-phenyl-1-(2-pyridyl)-4,4-dimethyl-3-pentanone First process:

There is maintained under reflux for 3 hours, 0.1 mole of the ketone of Example 1, 0.1 mole dimethylaminoethoxyamine hydrochloride in solution in 150 ml anhydrous ethanol in the presence of 75 ml pyridine. This is concentrated, made alkaline and extracted with benzene. The yield is 65%.

Second process:

There is added slowly 1.4 g 50% sodium hydride in oil to a solution of 0.03 mole of the oxime of Example 1 in dimethylformamide. There is then added 0.03 mole 2-chloro-ethyldiethylamine. After 6 hours of stirring at 70° C., the solution is poured into water. This is extracted with ether, dried and cncentrated, the yield is 51%. The formula, physical constants and results of tests for spasmolytic and anti-histamine effect of the product obtained are indicated in Table II below.

EXAMPLES 8 to 18

The process of Example 7 is followed starting from ketones or oximes of Examples 1 to 6 and corresponding amino-alkoxyamine derivatives. The formulae, physical constants and results of tests for spasmolytic and anithistamine effect are indicated in Table II below.

The compounds prepared are:

EXAMPLE 8
O-(Dimethylaminoethyl)-ether of the oxime of 1-phenyl-1-(2-pyridyl)-4,4-dimethyl-3-pentanone.

EXAMPLE 9
O-(Diisopropylaminoethyl)-ether of the oxime of 1-phenyl-1-(2-pyridyl)-4,4-dimethyl-3-pentanone.

EXAMPLE 10
O-(Pyrrolidinoethyl)-ether of the oxime of 1-phenyl-1-(2-pyridyl)-4,4-dimethyl-3-pentanone.

EXAMPLE 11
O-(Dimethylaminopropyl)-ether of the oxime of 1-phenyl-1-(2-pyridyl)-4,4-dimethyl-3-pentanone.

EXAMPLE 12
O-(Diethylaminoethyl)-ether of the oxime of 1-(4-chloro-phenyl)-1-(2-pyridyl)-4,4-dimethyl-3-pentanone.

EXAMPLE 13
O-(N-morpholinoethyl)-ether of the oxime of 1-phenyl-1-(2-pyridyl)-4,4-dimethyl-3-pentanone.

EXAMPLE 14
O-(N-methylpiperazinoethyl)-ether of the oxime of 1-phenyl-1-(2-pyridyl)-4,4-dimethyl-3-pentanone.

EXAMPLE 15
O-(Diethylaminoethyl)-ether of the oxime of 1-cyclohexyl-1-(2-pyridyl)-4,4-dimethyl-3-pentanone.

EXAMPLE 16
O-(Diethylaminoethyl)-ether of the oxime of 1-benzyl-1-(2-pyridyl)-4,4-dimethyl-3-pentanone.

EXAMPLE 17
O-(Diethylaminoethyl)-ether of the oxime of 1-phenyl-1-(3-pyridyl)-4,4-dimethyl-3-pentanone.

EXAMPLE 18
O-(Diethylaminoethyl)-ether of the oxime of 1-phenyl-1-(4-pyridyl)-4,4-dimethyl-3-pentanone.

From the results of the pharmacological tests of Table II there can be seen that the compounds display interesting activity.

TABLE II

| Ex | General formula I | | | | | Boiling point Bp: °C./mmHg and/or Melting point of hydrochloride Mp: °C. | Acetylcholine | | $BaCl_2$ | | Histamine | |
|---|---|---|---|---|---|---|---|---|---|---|---|---|
| | $R_1$ | $R_2$ | $R_3$ | $R_4$ | n | | $C_1$ | $ED_{50}$ | $C_2$ | $ED_{50}$ | $C_3$ | $ED_{50}$ |
| 7 | phenyl | 2-pyridyl | $CH_3CH_2-$ | $CH_3CH_2-$ | 2 | 182/0.15 Mp: 110 | $5.10^{-8}$ | 49 | $5.10^{-7}$ | 66 | $5.10^{-7}$ | 46 |
| 8 | phenyl | 2-pyridyl | $CH_3-$ | $CH_3-$ | 2 | Mp: 170 | $5.10^{-9}$ $10^{-8}$ | 31 50 | | | $10^{-6}$ | 50 |
| 9 | phenyl | 2-pyridyl | $(CH_3)_2CH-$ | $(CH_3)_2CH-$ | 2 | 178/0.1 | $10^{-7}$ | 52 | $10^{-6}$ | 65 | $10^{-6}$ | 65 |
| 10 | phenyl | 2-pyridyl | pyrrolidino | | 2 | 196/0.2 Mp: 174 | $10^{-8}$ | 52 | $10^{-6}$ | 45 | $5.10^{-6}$ | 67 |
| 11 | phenyl | 2-pyridyl | $CH_3-$ | $CH_3-$ | 3 | 172/0.5 | $10^{-7}$ | 13 | $10^{-6}$ | 58 | $10^{-6}$ | 58 |
| 12 | 4-Cl-phenyl | 2-pyridyl | $CH_3CH_2-$ | $CH_3CH_2-$ | 2 | 190/0.08 | $5.10^{-7}$ | 44 | | | $10^{-6}$ | 42 |
| 13 | phenyl | 2-pyridyl | morpholino | | 2 | 187/0.1 | $10^{-7}$ | 21 | | | $10^{-6}$ | 48 |

TABLE II-continued

| Ex | General formula I R₁ | R₂ | R₃ | R₄ | n | Bp: °C./mmHg and/or Mp: °C. of hydrochloride | Acetylcholine $C_1$ | $ED_{50}$ | $BaCl_2$ $C_2$ | $ED_{50}$ | Histamine $C_3$ | $ED_{50}$ |
|---|---|---|---|---|---|---|---|---|---|---|---|---|
| 14 | phenyl | 2-pyridyl | \multicolumn{2}{l|}{N-methylpiperazino} | 2 | 192/0.07 | $10^{-6}$ | 41 | | | $10^{-6}$ | 43 |
| 15 | cyclohexyl | 2-pyridyl | $CH_3CH_2-$ | $CH_3CH_2-$ | 2 | 164/0.05 | $10^{-7}$ $10^{-6}$ | 12 73 | | | $10^{-6}$ | 47 |
| 16 | benzyl ($C_6H_5CH_2-$) | 2-pyridyl | $CH_3CH_2-$ | $CH_3CH_2-$ | 2 | 175/0.4 | $10^{-7}$ $10^{-6}$ | 18 64 | | | $10^{-5}$ | 73 |
| 17 | phenyl | 3-pyridyl | $CH_3CH_2-$ | $CH_3CH_2-$ | 2 | 162/0.025 | $10^{-7}$ $10^{-6}$ | 15 73 | | | $10^{-6}$ | 42 |
| 18 | phenyl | 4-pyridyl | $CH_3CH_2-$ | $CH_3CH_2-$ | 2 | 168/0.04 | $10^{-6}$ | 40 | | | $10^{-6}$ $5.10^{-6}$ | 22 95 |

Legend:
$C_1$, $C_2$, $C_3$: concentration in mole per 1 respectively of acetylcholine, barium chlorine and histamine provoking a contraction of the organ.
$ED_{50}$: Effective dose 50.

We claim:
1. An oxime ether of the formula I

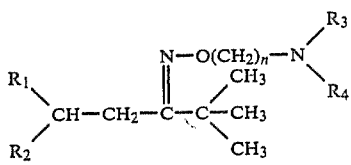

in which
R₁ is chosen from a cyclohexyl radical, or a phenyl or benzyl radical optionally substituted by a halogen atom or by a straight chain or branched alkyl radical having 1 to 4 carbon atoms,
R₂ is a pyridyl radical,
each of R₃ and R₄, which may be the same or different, represents a straight chain or branched alkyl radical having 1 to 4 carbon atoms, or
R₃ and R₄ taken togehter represent a pyrrolidino moiety, a morpholino moiety or a piperazino moiety and
n is an integer of 1 to 4, or a salt, quaternary ammonium derivative, or possible stereo-isomer or a mixture thereof of such an oxime ether.
2. An oxime ether according to claim 1 in which n is 2 or 3.
3. O-(Pyrrolidinoethyl)-ether of the oxime of 1-phenyl-1-(2-pyridyl)-4,4-dimethyl-3-pentanone according to claim 1.
4. O-(Diethylaminoethyl)-ether of the oxime of 1-phenyl-1-(2-pyridyl)-4,4-dimethyl-3-pentanone according to claim 1.
5. O-(Dimethylaminopropyl)-ether of the oxime of 1-phenyl-1-(2-pyridyl)-4,4-dimethyl-3-pentanone according to claim 1.
6. O-(Dimethylaminoethyl)-ether of the oxime of 1-phenyl-1-(2-pyridyl)-4,4-dimethyl-3-pentanone according to claim 1.
7. A pharmaceutical composition in dosage unit form which comprises an amount of a compound according to claim 1 effective as a spasmolytic, associated with a pharmaceutically acceptable vehicle.
8. O-(N-methylpiperazinoethyl)-ether of the oxime of 1-phenyl-1-(2-pyridyl)-4,4-dimethyl-3-pentanone.
9. A method for treating an animal in need of a spasmolytic which comprises administering a spasmolytically effective amount of a compound according to claim 1.

* * * * *